(12) United States Patent
Knodel et al.

(10) Patent No.: US 8,123,795 B1
(45) Date of Patent: Feb. 28, 2012

(54) SYSTEM FOR ATTACHING AN ABDOMINAL AORTIC STENT OR THE LIKE

(75) Inventors: Bryan D. Knodel, Flagstaff, AZ (US); David L. Bombard, San Francisco, CA (US); Theodore M. Bender, Oakland, CA (US); Luke W. Clauson, Redwood Shores, CA (US); Bernard A. Hausen, Redwood City, CA (US)

(73) Assignee: Cardica, Inc., Redwood City, CA (US)

( * ) Notice: Subject to any disclaimer, the term of this patent is extended or adjusted under 35 U.S.C. 154(b) by 392 days.

(21) Appl. No.: 11/542,294

(22) Filed: Oct. 3, 2006

Related U.S. Application Data (60) Provisional application No. 60/723,114, filed on Oct. 3, 2005.

(51) Int. Cl.
*A61F 2/06* (2006.01)

(52) U.S. Cl. .................... 623/1.23; 623/1.11

(58) Field of Classification Search ............ 623/1.11, 623/1.13, 1.15, 2.11, 23.64, 1.23; 606/144, 606/145, 157, 217, 218, 219, 220, 221, 232, 606/233, 139–143; 227/175.1, 175.2, 175.3, 227/175.4, 176.1, 177.1, 178.1, 179.1, 180.1, 227/181.1, 182.1, 82, 83
See application file for complete search history.

(56) References Cited

U.S. PATENT DOCUMENTS

| | | | | |
|---|---|---|---|---|
| 3,086,208 A | * | 4/1963 | Eby | 206/339 |
| 5,042,707 A | * | 8/1991 | Taheri | 606/213 |
| 5,289,963 A | * | 3/1994 | McGarry et al. | 227/175.1 |
| 5,381,943 A | * | 1/1995 | Allen et al. | 227/177.1 |
| 5,626,587 A | * | 5/1997 | Bishop et al. | 606/143 |
| 5,972,023 A | * | 10/1999 | Tanner et al. | 606/219 |
| 5,997,556 A | * | 12/1999 | Tanner | 606/153 |
| 6,070,589 A | * | 6/2000 | Keith et al. | 128/898 |
| 6,126,685 A | * | 10/2000 | Lenker et al. | 623/1.11 |
| 6,302,906 B1 | * | 10/2001 | Goicoechea et al. | 623/1.11 |
| 6,520,974 B2 | * | 2/2003 | Tanner et al. | 606/153 |
| 6,685,735 B1 | * | 2/2004 | Ahari | 623/1.11 |
| 6,800,081 B2 | * | 10/2004 | Parodi | 606/139 |
| 6,827,730 B1 | * | 12/2004 | Leschinsky | 623/1.11 |
| 2003/0023248 A1 | * | 1/2003 | Parodi | 606/139 |
| 2003/0032981 A1 | * | 2/2003 | Kanner et al. | 606/219 |
| 2003/0100943 A1 | * | 5/2003 | Bolduc | 623/1.35 |
| 2003/0187465 A1 | * | 10/2003 | Bailly et al. | 606/143 |
| 2003/0195607 A1 | * | 10/2003 | Trout et al. | 623/1.13 |
| 2004/0176663 A1 | * | 9/2004 | Edoga et al. | 600/139 |
| 2005/0004582 A1 | * | 1/2005 | Edoga et al. | 606/139 |
| 2005/0015100 A1 | * | 1/2005 | Parodi | 606/139 |
| 2005/0090834 A1 | | 4/2005 | Chiang et al. | |
| 2005/0090843 A1 | | 4/2005 | Bolduc | |

(Continued)

*Primary Examiner* — S. Thomas Hughes
*Assistant Examiner* — David Eastwood
(74) *Attorney, Agent, or Firm* — Brian A. Schar (57) ABSTRACT

A surgical tool useful for connecting an abdominal aortic stent or the like to tissue may include a head holding at least one fastener, a shaft, and a joint connecting the head to the shaft, the joint allowing the head to rotate in at least one direction relative to the shaft. That surgical tool may be used to connect a graft assembly to tissue, where the graft assembly may include a graft connected to a stent. The graft, stent and surgical tool may be inserted into a body lumen; and the head of the surgical tool may be pivoted relative to the shaft such that the distal end of the head contacts the interior of the stent. At least one fastener is then deployed to connect the stent to the body lumen.

8 Claims, 10 Drawing Sheets

U.S. PATENT DOCUMENTS

2005/0107812 A1* 5/2005 Starksen et al. .............. 606/143
2005/0187613 A1* 8/2005 Bolduc et al. ................ 623/1.23
2005/0216036 A1* 9/2005 Nakao .......................... 606/142
2006/0241656 A1* 10/2006 Starksen et al. .............. 606/143

* cited by examiner

SYSTEM FOR ATTACHING AN ABDOMINAL AORTIC STENT OR THE LIKE

This application claims priority to U.S. Provisional Patent Application Ser. No. 60/723,114, filed on Oct. 3, 2005, which is hereby incorporated by reference in its entirety.

FIELD OF THE INVENTION

The invention relates to an apparatus and method for attaching an abdominal aorta stent or the like to a patient.

BACKGROUND

Abdominal aortic aneurysm (AAA) is an abnormal ballooning of the abdominal portion of the aorta, which is the major artery routing blood from the heart to all organs. Abdominal aortic aneurysm involves a dilation, stretching, or ballooning of the abdominal aorta, which is the section of the aorta residing in the abdominal cavity. Causes of abdominal aortic aneurysm include infection, tissue disease (such as atherosclerosis) resulting in weakening of the connective tissue component of the arterial wall, trauma, and Marfan's syndrome. Abdominal aortic aneurysm can affect anyone, but it is most often seen in men aged 40 to 70. Most commonly, abdominal aortic aneurysms occur in the portion of the vessel below the renal artery origins, and may extend into the vessels supplying the hips and pelvis.

A common complication of AAA is rupture. This is a medical emergency where the aneurysm breaks open, resulting in profuse bleeding. Aortic rupture is life-threatening; the likelihood of death after rupture is generally considered to be 80-90%. Once an aneurysm reaches 5 cm in diameter, it is usually considered necessary to treat it to prevent rupture.

Surgical repair or replacement of the section of aorta that includes the aneurysm is recommended for patients with symptoms and for patients with aneurysms greater than 5 cm in diameter, as they are at high risk of fatal rupture. Because surgery for abdominal aortic aneurysm is risky, the surgeon may wait for the aneurysm to expand to a size at which the risk of complications exceeds the risk of surgery. Below 5 cm, the risk of the aneurysm rupturing is lower than the risk of conventional surgery in patients with normal surgical risks. However, it is undesirable to wait for a known AAA to get worse in order to treat it.

Placement of an AAA graft is also a treatment option. An AAA graft is a tube or tubelike structure placed inside the aorta. Its placement can be performed without an abdominal incision, with specialized catheters that are introduced through arteries at the groin. However, not all patients with abdominal aortic aneurysms are candidates for grafts, however. Further, some AAA grafts in the past have had difficulties that have resulted in their removal from the marketplace, such as breakage of the hooks that hold the AAA graft in place in the aorta, and difficulties with the tools for deploying the AAA grafts.

DETAILED DESCRIPTION

U.S. patent application Ser. Nos. 11/093,003, 11/022,551, 11/158,413, and 11/158,414 are incorporated herein by reference in their entirety.

Figure 1:
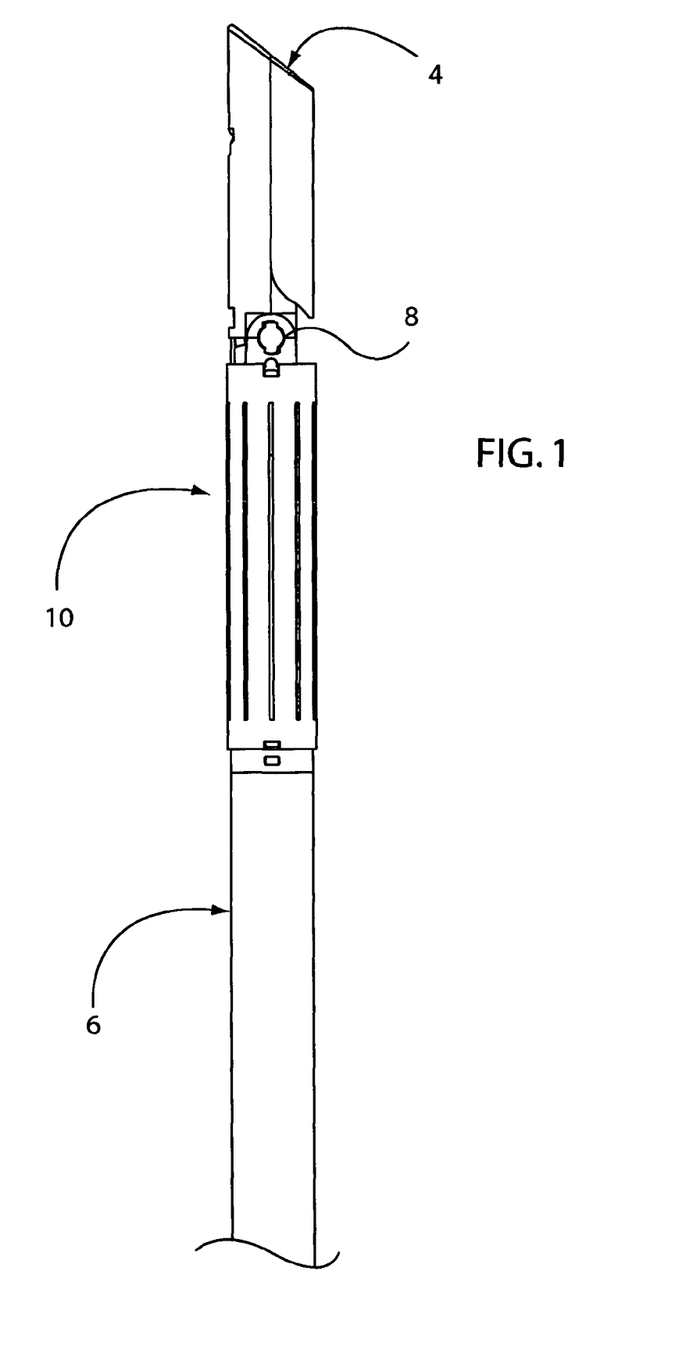
FIG. 1 is a side view of the end of a stapling tool in a first, insertion configuration.
Figure 2:
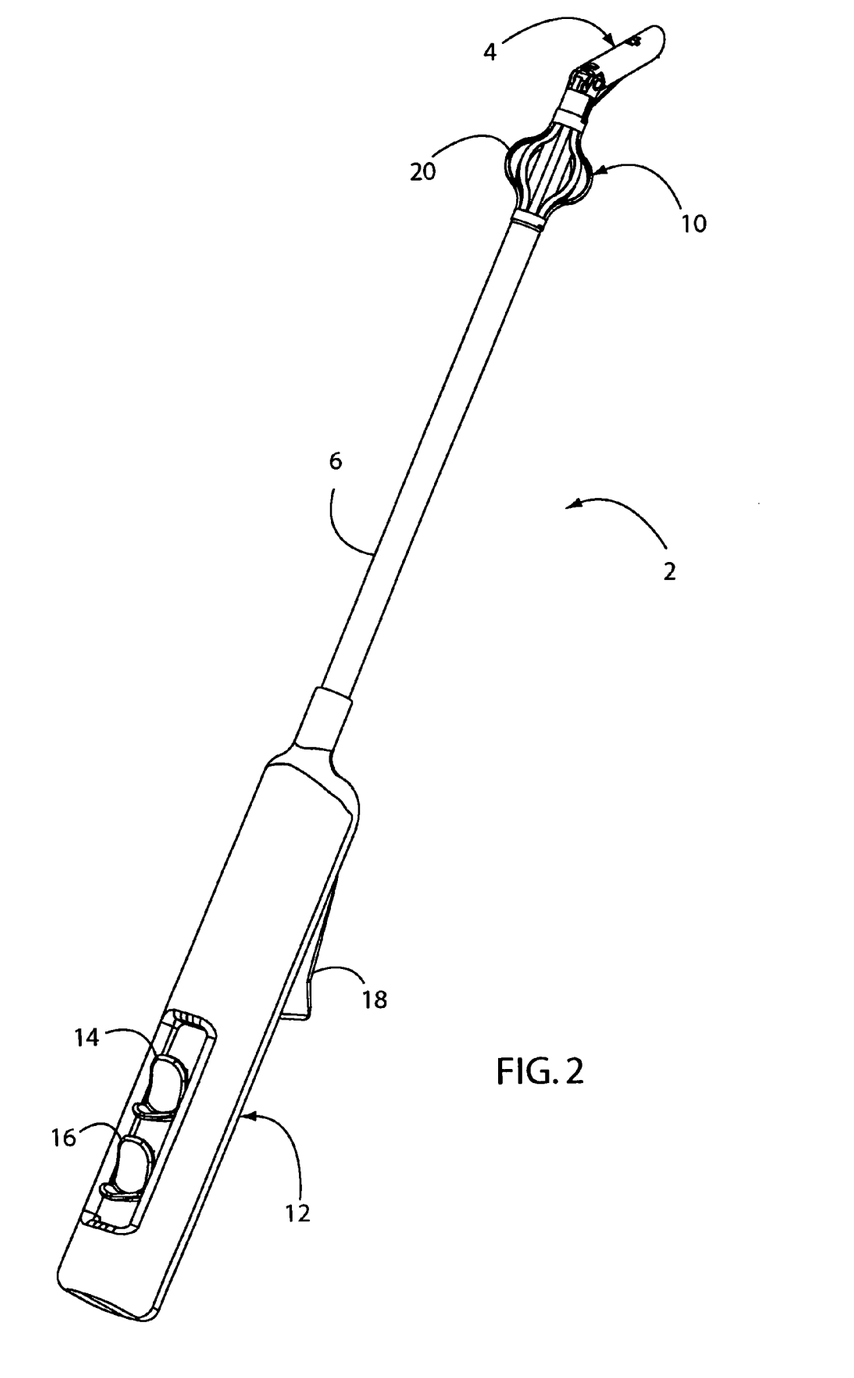
FIG. 2 is a perspective view of a stapling tool, the end of which is shown in FIG. 1, in a second, stapling configuration.
Figure 3:
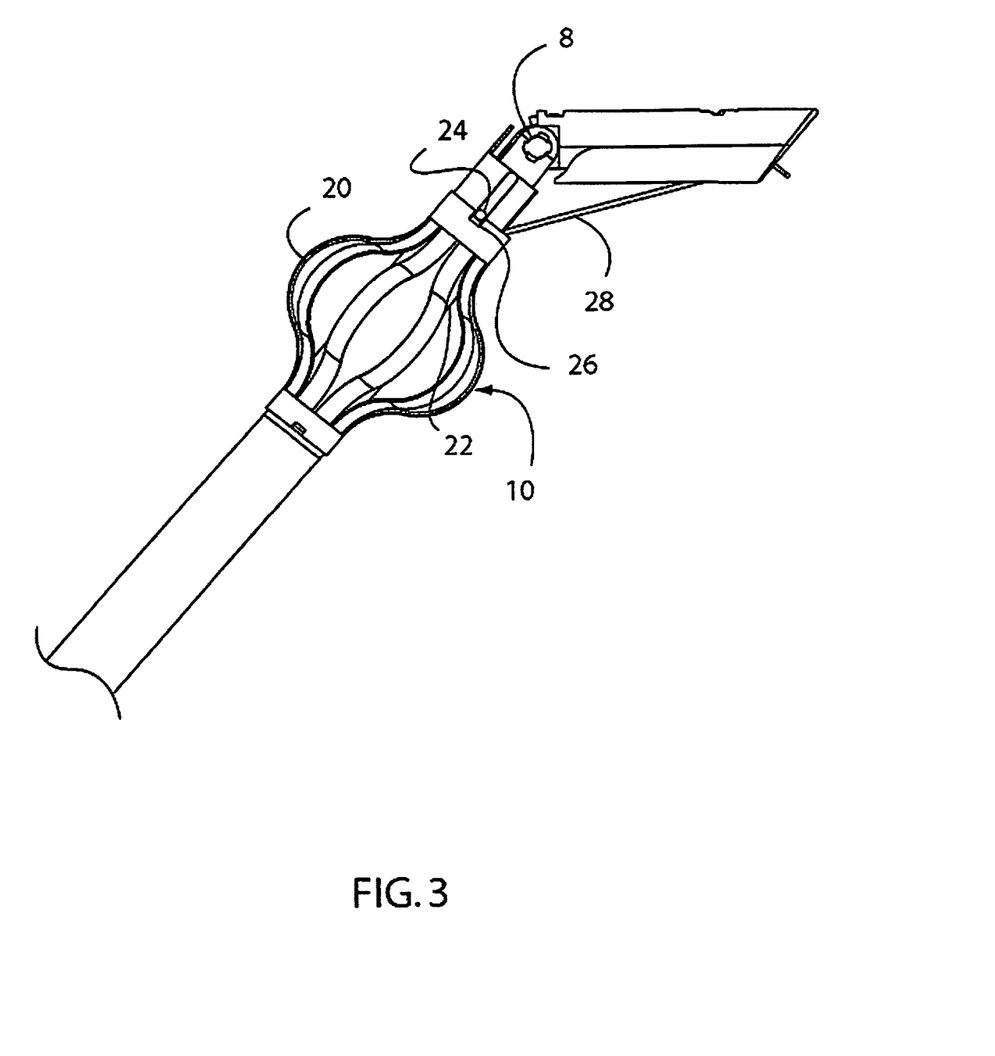
FIG. 3 is a side view of the end of the stapling tool of FIG. 2.

Referring to FIG. 1, a head 4 is attached to a shaft 6 via a joint 8. The head 4 may be configured to deploy one or more fixation devices, such as staples, clips, barbs, or any other suitable device or devices. The head 4 is described in greater detail below. Referring also to FIG. 2, the shaft 6 extends proximally from the head 4 to a handle 12. At least part of the shaft 6 is flexible, to allow the shaft 6 to be inserted through an opening in the patient's femoral artery or other access point in the vasculature and advanced through the vasculature to a treatment site. The joint 8 allows the head 4 to rotate in at least one direction relative to the shaft 6. The joint 8 may be a pin, hinge, ball joint, swivel joint, or any other suitable mechanism. A stabilizer 10 may be positioned at or near the distal end of the shaft 6. The stabilizer 10 is movable between an initial insertion configuration as shown in FIG. 1, and a second expanded configuration as shown in FIGS. 2-3. The stabilizer 10 may be a substantially cylindrical element having one or more slits 11 defined substantially longitudinally therein. Alternately, the slits 11 may be oriented differently, or omitted. An inner shaft 22 as shown in FIG. 3 may push proximally on the distal end of the stabilizer 10 while the shaft 6 holds the proximal end of the stabilizer 10, in order to impart a compressive force to the stabilizer 10 and expand it. For example, at least one pin 24 extending from the inner shaft 22 engages a corresponding notch 26 in the distal end of the stabilizer 10. The ribs 20 between the slits 11 bow outward under that compressive force, such that the stabilizer 10 expands to the expanded configuration. The expanded configuration of the stabilizer 10 has a diameter substantially the same as, or greater than, the aorta or other vessel in which the head 4 is to be used. Alternately, the stabilizer 10 may be expanded differently. Alternately, the stabilizer 10 may include other or additional structures or mechanisms, and/or may be operated in a different manner.

The stabilizer 10 may be connected, physically or operationally, to the stabilizer control 14 on the handle 12 of the fastening tool 2. For example, a cable or other suitable mechanism may extend from the handle 12 to the distal end of the stabilizer 10 and/or to the inner shaft 22 in proximity to the distal end of the stabilizer 10, such that upon actuation of the stabilizer control 14, the cable moves proximally and causes a proximal force to be exerted on the distal end of the stabilizer 10. The stabilizer control 14 may be operated in any suitable manner. As one example, the stabilizer control 14 may be moved proximally a distance along the handle 12 that corresponds with the distance the distal end of the stabilizer 10 travels during expansion. As another example, the handle 12 may include a source of stored energy, such as a spring, compressed gas, vacuum, or any other suitable energy source. Upon actuation of the stabilizer control 14, the stabilizer control 14 may release energy from the source of stored energy, such that the released energy pulls the cable or other suitable mechanism that expands the stabilizer 10.

Referring also to FIGS. 2-3, a cable 28 extends distally from the shaft 6 to connect with the head 4. The shaft 6 includes at least one lumen therein; the cable 28 extends from the handle 12 to the head 4 through one such lumen. Alternately, the cable 28 may run along the exterior of the shaft 6 or be positioned in some other manner. The cable 28 may be fixed at one end to the head 4, and movable at the other end. By moving the proximal end of the cable 28 proximally and applying tension to it, the head 4 swivels about the joint 8 from a first, initial position to a second, deployment position. In the first position, the head 4 may have a longitudinal centerline substantially collinear with the longitudinal centerline of the shaft 6; in the second position, the longitudinal centerline of the head 4 may be angled relative to, and intersect, the longitudinal centerline of the shaft 6. Alternately, the head 4 and shaft 6 may have a different spatial relationship relative to one another when the head 4 is in the initial position and/or in the deployment position. Tension may be applied to the cable 28 by actuation of the head swivel control 16 on the handle 12. Such tension may be applied to the cable 28 in any suitable manner, such as described above with regard to tensioning of a cable by the stabilizer control 14

Figure 4:
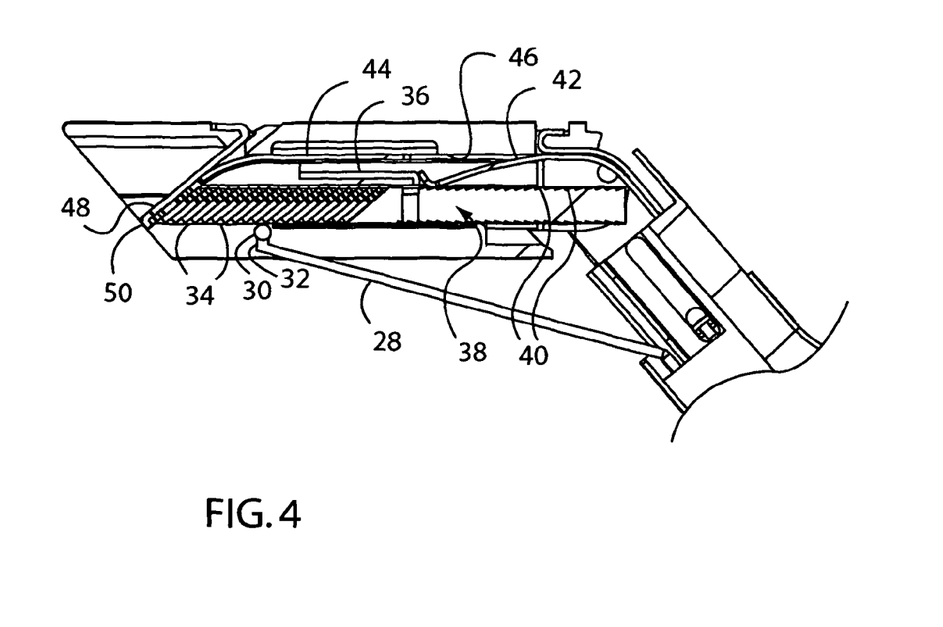
FIG. 4 is a side cutaway view of a stapler head of the stapling tool of FIG. 2.

Referring to FIG. 4, the cable 28 may be attached to the head 4 in any suitable manner. As one example, a ball 30 is attached to the distal end of the cable 28, where the ball 30 has a wider diameter than a passage 32 in the head 4 through which the cable 28 passes. Interference between the ball 30 and the passage 32 when the cable 28 is tensioned results in the application of force to the head 4.

Figures 13A, 13B:
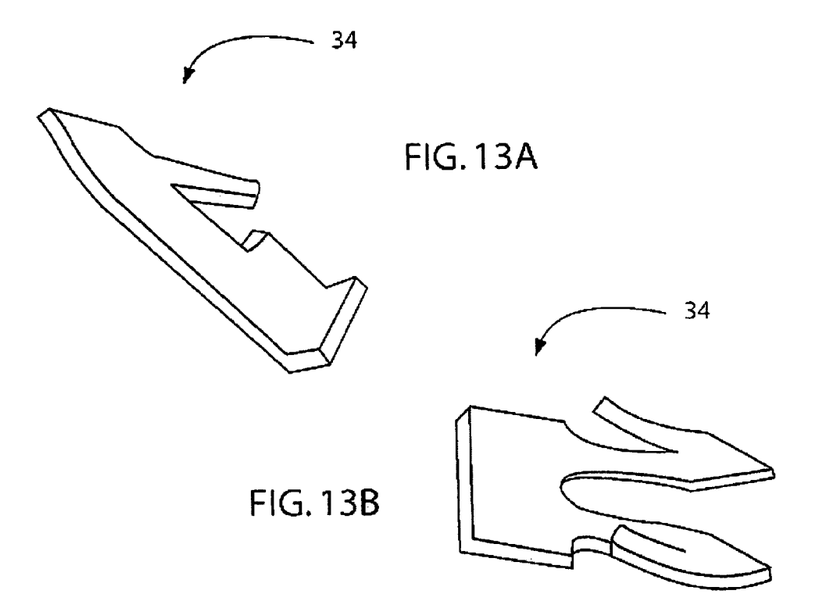
FIG. 13 is a collection of views of exemplary barbs that may be deployed in the fourth step illustrated in FIG. 10.
Figure 13C:
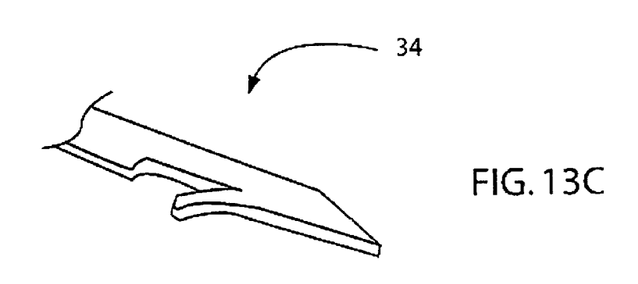
Figure 13D:
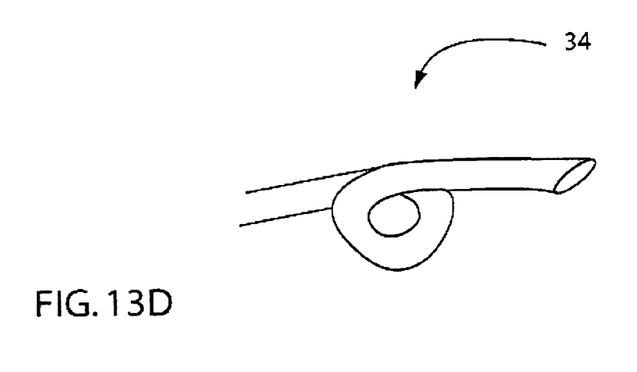
Figure 14A:
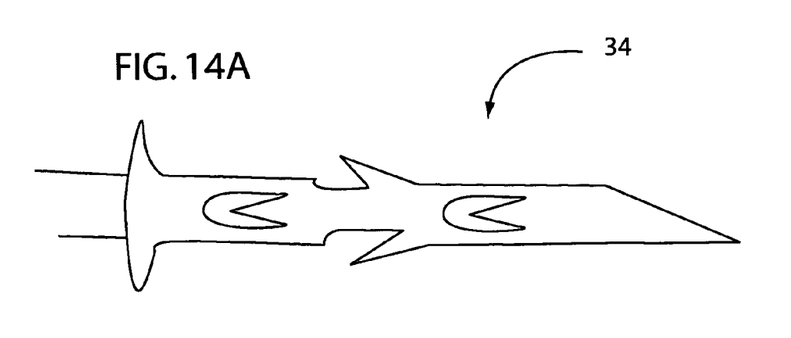
FIG. 14 is a second collection of views of exemplary barbs that may be deployed in the fourth step illustrated in FIG. 10.
Figure 14B:
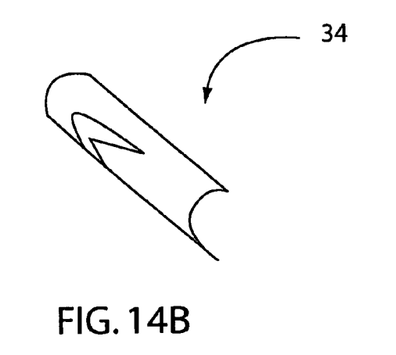
Figure 14C:
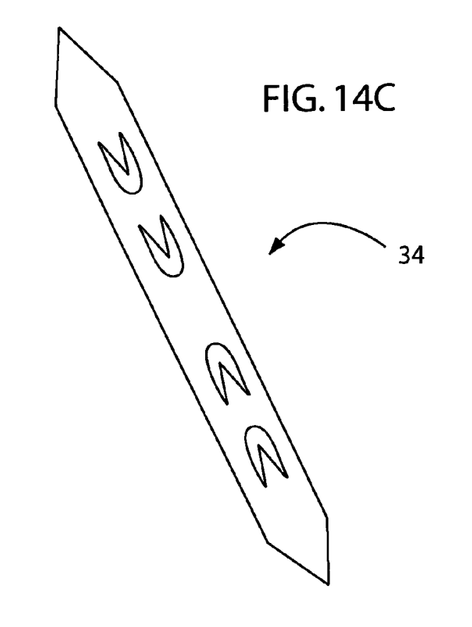
Figure 14D:
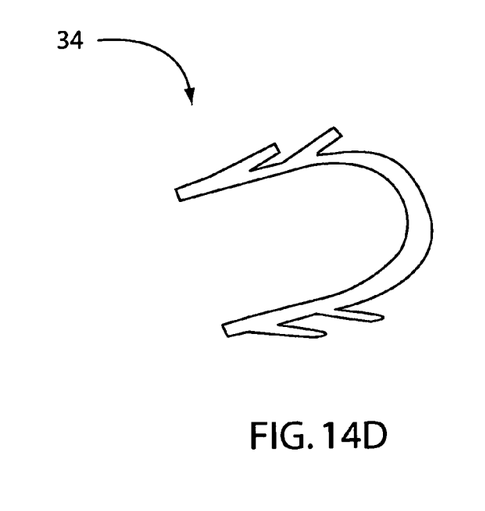

One or more fasteners 34 are held within the head 4. Alternately, one or more fasteners 34 are held in the shaft 6 and/or in one or more components connected to the head 4, and fed into the head 4 as needed. Where multiple fasteners 34 are provided, they may all be of the same type, or may be of different types. As one example, the fasteners 34 are conventional wire staples. As another example, the fasteners are staples as disclosed in U.S. patent application Ser. Nos. 11/022,551 and 11/158,413. As another example, the fasteners are staples as disclosed in U.S. patent application Ser. Nos. 11/093,003 and 11/158,414. As another example, the fasteners 34 may be clips. As another example, the fasteners 34 may be staples as shown in FIG. 12. As another example, the fasteners 34 may be barbs as shown in FIGS. 13-14. As another example, the fasteners 34 may be any other suitable structures or mechanisms for fastening an AAA graft or other therapeutic device to a blood vessel or other structure in a patient.

Where multiple fasteners 34 are used, they may be held within a rack 36. The rack 36 may be a cartridge that is detachable from the remainder of the tool 2 and replaceable with a fresh cartridge, such that the tool 2 is reusable. As another example, the rack 36 may be held permanently within the head 4, such that the tool 2 is suitable for a single use. The tool 2 may be easier to fabricate if the rack 36 is held permanently within the head 4. The rack 36 may be slidable along a cavity 38 in the head 4. The cavity 38 may be oriented in a direction substantially along or parallel to the longitudinal centerline of the head 4. Alternately, the cavity 38 may be oriented in a different manner. The cavity 38 may include one or more teeth 40 or other elements configured to engage the rack 36 and restrain it from sliding freely within the cavity 38. The teeth 40 may be preferentially deflectable such that engagement between the rack 36 and the teeth 40 only allows the rack 36 to travel distally. Alternately, the teeth 40 are not preferentially deflectable. Alternately, the teeth 40 are not deflectable. Advantageously, the teeth 40 are spaced apart from one another a distance substantially equal to the thickness of one fastener 34. In this way, the rack 36 easily can be advanced one fastener 34 at a time, by advancing the rack 36 ahead by one row of teeth 40. A pusher 42 may extend along the shaft 6 into the head 4. The pusher 42 may be a long, thin strip of spring steel. Alternately, the pusher 42 may be shaped in any other suitable manner and/or fabricated from any other suitable material. The distal end of the pusher 42 contacts the rack 36 in any suitable manner. The distal end of the pusher 42 may be adjacent to the rack 36 without being connected to it, or may be connected to the rack 36. As one example, the distal tip of the pusher 42 may be angled relative to an adjacent portion of the pusher 42, and that angled distal tip of the pusher 42 may contact the rack 36. Distal advancement of the pusher 42 in turn pushes the rack 36 distally.

Figure 5:
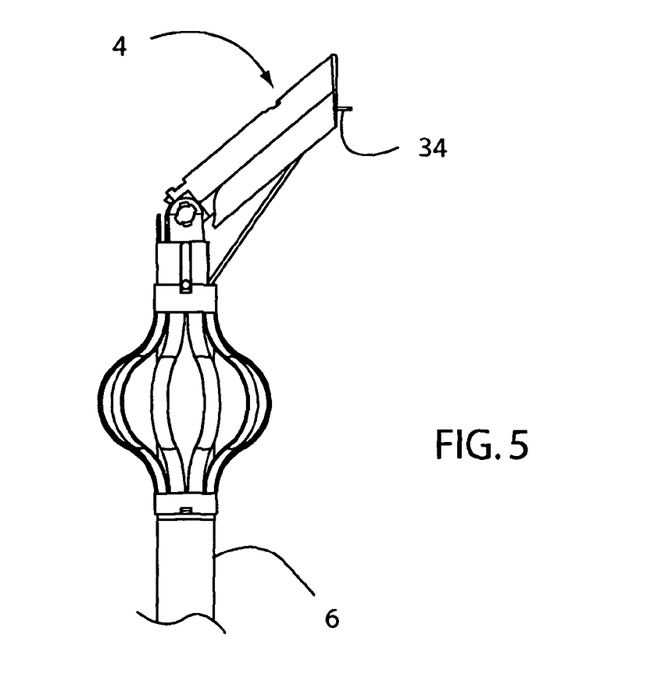
FIG. 5 is a side view of the stapler head of the stapling tool of FIG. 2, showing a staple being deployed from the stapler head.

A driver 44 also extends along the shaft 6 into the head 4. The driver 44 may be a long, thin strip of spring steel. Alternately, the driver 44 may be shaped in any other suitable manner and/or fabricated from any other suitable material. The distal portion of the driver 44 may be positioned within a slot 46 defined in the head 4. The slot 46 may be a portion of the cavity 38, may be defined in one or more surface of the cavity 38, or may be separate from the cavity 38, as desired. The slot 46 is shaped to guide the distal end of the driver 44 into contact with a fastener 34 to allow the driver 44 to deploy the fastener 34, as described in greater detail below. The driver 44 may be actuated in any suitable manner by a trigger 18 or other mechanism positioned in and/or on the handle 12. For example, the driver 44 may be pushed distally in any suitable manner, such as by the release of stored energy, or by a mechanism directly linked to the travel of the trigger 18. A backstop 48 may be positioned in the head 4 distal to the rack 36. The lower edge of the backstop 48 may include an anvil 50. The backstop 48 may assist in holding the most-distal fastener 34 in place prior to its deployment. The anvil 50 provides a point for a fastener 34 to deform about during deployment. The backstop 48 may be configured to bend away from the rack 36 upon distal motion of the driver 34, such as upon contact between the driver 34 and the backstop 48, thereby moving the anvil 50 out of the ejection path of the fastener 34 after the fastener 34 has been deformed. Alternately, the anvil 50 may be omitted where the fasteners 34 are superelastic, or are barbs or other fasteners 34 that do not substantially deform upon deployment. Referring also to FIG. 5, the head 4 may be angled relative to the shaft 6 using the cable 28 or any other suitable mechanism, and the fasteners 34 may be angled within the head 4, such that the fasteners 34 can be deployed in a direction substantially perpendicular to the longitudinal centerline of the shaft 6. Alternately, the head 4 may be configured such that the fasteners 34 are deployed at any other suitable angle relative to the shaft 6. At least one fastener 34 may lie in a plane that is oriented at a non-orthogonal angle to the longitudinal centerline of the head 4, as shown in FIG. 4.

In an alternate embodiment, the head 4 of the fastening tool 2 instead includes a plurality of arms movable from a first, insertion configuration in which the arms are collapsed toward one another, and a second, deployed configuration in which at least part of each arm is spaced further apart from the other arms. Each arm may hold one or more fasteners 34. Each arm acts to stabilize the others relative to the aorta 70, and also is configured to deploy at least one fastener 34. Alternately, at least one arm is a stabilizer that does not deploy at least one fastener 34. The fasteners 34 used with the arms may be configured such that they need not be deformed in order to connect the graft 54 to the aorta 70. Such fasteners 34 may be utilized with any embodiment of the head 4 of the fastening tool 2.

Figure 6:
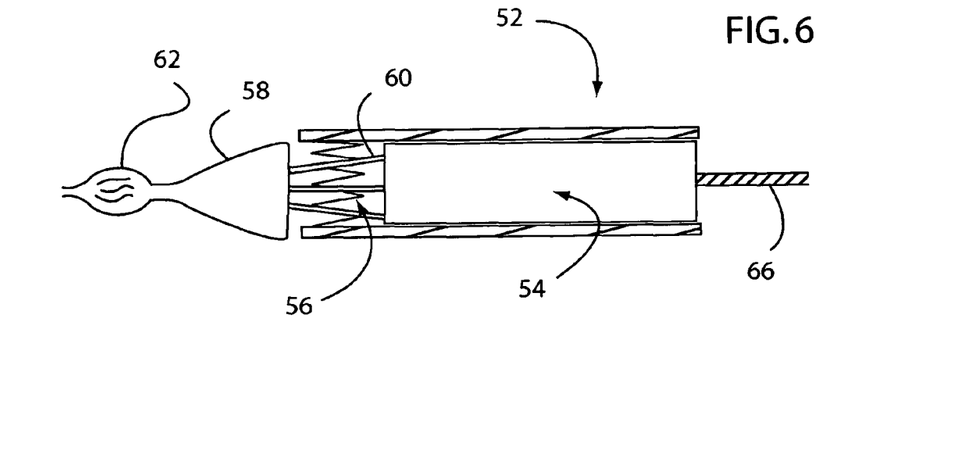
FIG. 6 is a side cutaway view of an assembly introducible into a patient, where that assembly includes an AAA graft.

Referring to FIG. 6, a graft assembly 52 is used in conjunction with the fastening tool, as described in greater detail below. The graft assembly 52 includes an AAA graft 54, fabricated from DACRON® brand polyester, expanded polytetrafluoroethylene, or any other suitable material. A stent 56 is positioned distal to the graft 54, and may be spaced apart from the graft 54 and coaxial with it. By spacing the stent 56 apart from the graft 54, the diameter of the graft assembly 52 is less than it would be if part of or all of the stent 56 were within the graft 54. Alternately, at least part of the stent 56 may be positioned within the graft 54, and may be oriented other than coaxially relative to the graft 54. The stent 56 may be fabricated from any suitable material, such as nickel-titanium alloy, stainless steel, or ELGILOY® brand alloy. The stent 56 may be configured in any suitable manner, such as a zigzag configuration of bars. The stent 56 may be similar in configuration to the types of AAA fixation stents used in known AAA grafts, if desired.

A nose cone 58 may be positioned distal to the stent 56. The nose cone 58 optionally may be formed in a shape other than substantially conical. The nose cone 58 may be connected frangibly to the stent 56 by one or more struts 60. As one example, at least one strut 60 includes a weakened area that is smaller in cross-section that a remainder of the strut 60, such that the strut 60 breaks at the weakened area in response to a force. As another example, at least one strut 60 is connected to the stent 56 such that the strut 60 separates from the stent 56 in response to a force. In such an example, the strut 60 itself need not be frangible or breakable. A balloon 62 is connected to the nose cone 58, and may be positioned at the distal end of the nose cone 58. The balloon 62 may be fabricated from any suitable material. Optionally, the balloon 62 and nose cone 58 may be a single structure, part of which is inflatable. The balloon 62 is initially in a deflated state, and is inflatable to an expanded state. A tube (not shown) is connected to the balloon 62 and extends away from the graft assembly 52. The tube carries saline solution, pressurized gas or any other substance used to inflate the balloon 62, as described in greater detail below.

The graft assembly 52 may include at least one sheath 64 that extends around at least part of the stent 56 and the graft 54. Alternately, the sheath 64 may be longer or shorter, or extend around more or fewer components. Alternately, the sheath 64 may be omitted. The graft assembly 52 may be slidable along a guidewire 66.

In its initial, delivery configuration, the graft assembly 52 advantageously is no greater than 14 French in diameter, such that it can be shuttled through a catheter having an internal diameter of no greater than 14 French. In this way, a catheterization sheath having a size similar to that used for the placement of stents in the coronary arteries can be used. As a result, the hole made in the femoral artery or other vessel for introducing the catheter and the graft assembly 52 into the patient may be smaller than is currently required for introduction of AAA graft devices, which is typically 22 French. The hole in the blood vessel required for receiving a 22 French catheter is typically made with a full cutdown, which would not be required for a 14 French catheter.

Operation

Figure 7:
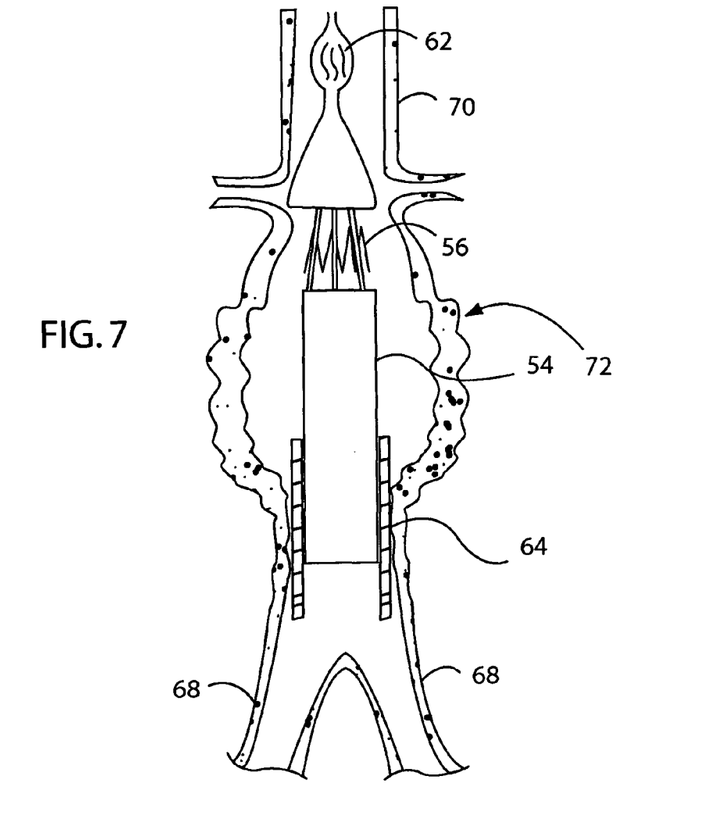
FIG. 7 is a side view of a first step of deploying an AAA graft.

The operation described below is in regard to the placement and fixation of an AAA graft at the site of an abdominal aortic aneurysm. However, this does not limit the usage of the fastening tool 2 or the graft assembly 52 to the repair of abdominal aortic aneurysms. The procedure may be performed under a fluoroscope to allow the operator to visualize the locations of the various components used therein within the body of the patient. Initially, referring also to FIG. 7, the guidewire 66 is introduced into the femoral artery 68 via an opening therein. The guidewire 66 is advanced along the femoral artery 68, then into the aorta 70, past the location of the abdominal aortic aneurysm 72. The guidewire 66 is then left in place. Next, the graft assembly 52 is advanced into the femoral artery 68 along the guidewire 66, until at least part of the stent 56 is positioned at a location retrograde to the abdominal aortic aneurysm 72. This position is selected such that, upon deployment, at least part of the stent 56 will engage tissue of the aorta 70 that is healthier than the tissue of the abdominal aortic aneurysm 72. The sheath 64 is then retracted proximally along the guidewire 66. The sheath 64 may be removed completely from the patient at this time, or may remain in the aorta 70 and/or femoral artery 68 at a location spaced apart from the graft assembly 52.

Figure 8:
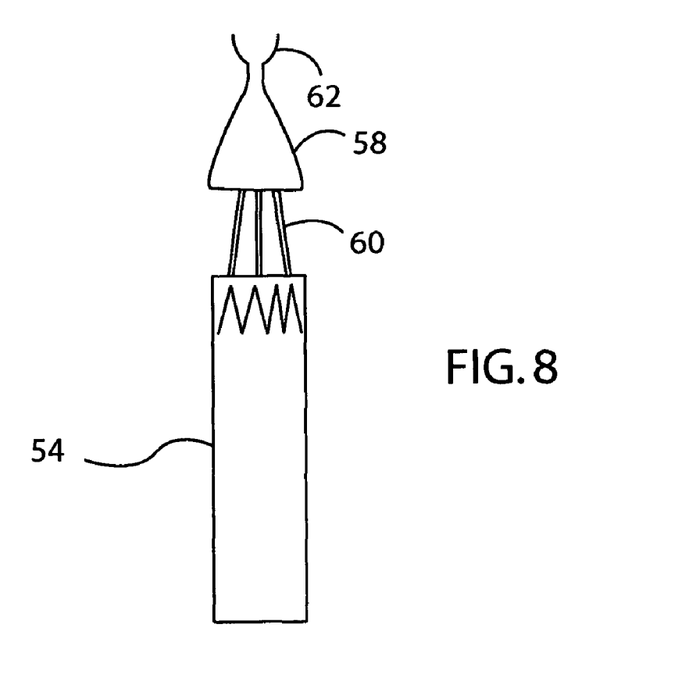
FIG. 8 is a side view of a second step of deploying an AAA graft.

Next, the balloon 62 is inflated. Alternately, the balloon 62 may be inflated before the sheath 64 is withdrawn. The balloon 62 is inflated to a diameter at least as great as the inner diameter of the aorta 70. The walls of the aorta 70 are somewhat elastic, allowing the balloon 62 to inflate to a diameter larger than the diameter of the aorta 70; the aorta 70 simply expands as well. As a result, the balloon 62 exerts a force on the inner walls of the aorta 70 that both holds the balloon 62 substantially in place relative to the aorta 70 and substantially stops blood flow through the aorta 70. The sheath 64 is then removed, exposing the remainder of the graft assembly 52. Alternately, the sheath 64 may be removed before the balloon 62 is inflated. Referring also to FIG. 8, the stent 56 is then lowered into the distal end of the lumen of the graft 54 in any suitable manner. The graft 54 continues to be connected to the nose cone 58 by at least one strut 60.

Figure 9:
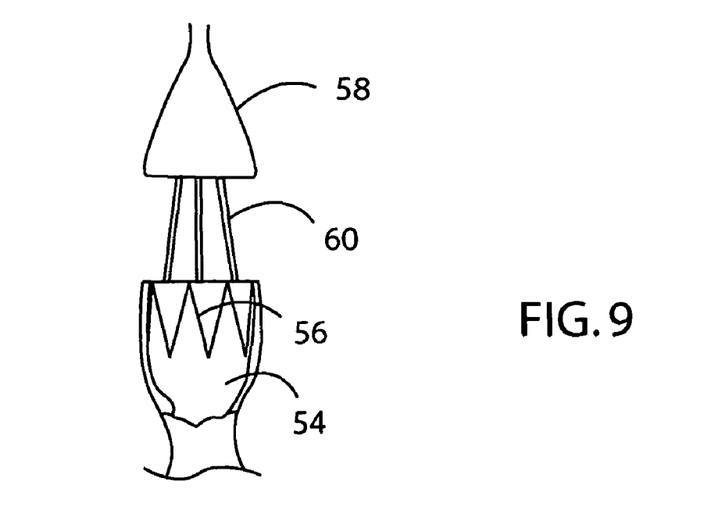
FIG. 9 is a side view of a third step of deploying an AAA graft.

Referring to FIG. 9, the diameter of the stent 56 is enlarged after its placement in the lumen of the graft 54. This enlargement may be accomplished in any suitable manner. As one example, the stent 56 may be fabricated from nickel-titanium alloy or other superelastic material, such that it self-expands to an enlarged configuration having a larger diameter upon release. As another example, the stent 56 may be plastically deformable, such that it is enlarged as a result of force being applied to it, such as by the balloon 62, by a different balloon (not shown) within the graft assembly 52, or by an expander (not shown) used in conjunction with the graft assembly 52. The stent 56 is expanded to a diameter at least as great as the inner diameter of the aorta 70, such that the stent 56 presses a portion of the graft 54 into contact with the aorta 70. The stent 56 may stretch at least part of the fabric of the graft 54, which is configured to allow such stretching. Optionally, the stent 56 may include one or more hooks, barbs or other engagement elements that engage the wall of the aorta 70, directly or through the fabric of the graft 70.

Figure 10:
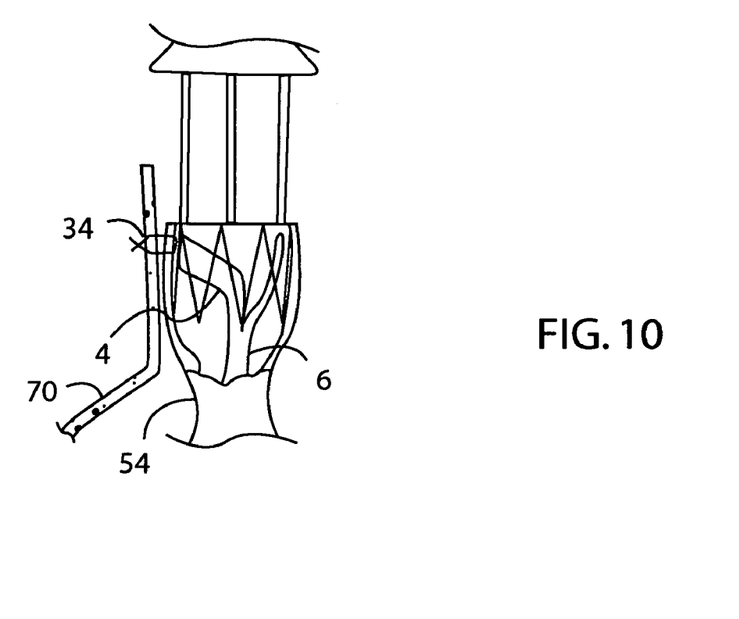
FIG. 10 is a side view of a fourth step of deploying an AAA graft.

Referring also to FIG. 10, the distal end of the fastening tool 2 is introduced into the patient, and the head 4 is advanced to the location of the stent 56 such as by pushing on the shaft 6. The head 4 may be in the initial position during that advancement. Next, the stabilizer control 14 is actuated, and the stabilizer 10 expands from its initial insertion configuration as shown in FIG. 1 to its second, expanded configuration as shown in FIGS. 2-3. The diameter of the stabilizer 10 is at least as great as the inner diameter of the aorta 70, such that in the expanded configuration it contacts and exerts a force against the aorta 70. In this way, the shaft 6 and head 4 of the fastening tool 2 are stabilized relative to the aorta.

Next, the cable 28 is retracted proximally, such as by actuation of the head swivel control 16. As a result, the head 4 rotates about the joint 8 to the second, deployment position. In this position, the fasteners 34 held by the head 4 are oriented generally perpendicular to the wall of the aorta 70. Alternately, one or more of the fasteners are oriented differently relative to the wall of the aorta 70. The head 4 is moved into proximity with a location on the stent 56. The operator then actuates the trigger 18, which pushes the driver 44 distally. The driver 44 may be pushed distally in any suitable manner, such as by the release of stored energy, or by a mechanism directly linked to the travel of the trigger 18. As the trigger 18 moves distally, it urges the driver 44 distally, which in turn pushes a fastener 34 into contact with the anvil 50, causing it to deform. The fastener 34 may be shaped such as set forth in U.S. patent application Ser. No. 11/093,003, such that it first splays before closing. After the fastener 34 has completed its deformation, it is released from the head 4, or may be actively ejected from the head 4 such as by a force exerted by the backstop 48. Alternately, at least one fastener 34 may be deployed in a different manner. For example, the fasteners 34 may be configured to penetrate the graft 54 and enter the wall of the aorta 70, and fix the graft 54 to the aorta 70, without deformation of the fasteners 34. The driver 44 is then retracted proximally. Next, the pusher 42 pushes the rack 36 distally, indexing it forward such that the next fastener 34 is position for deployment. Advantageously, the distal advancement of the driver 44, followed by the proximal retraction of the driver 44 and the advancement of the rack 36, all result from a single depression of the trigger 18, or from a single input to any other input mechanism of the fastening tool 2.

The fastener 34 may be placed such that it captures a portion of the stent 56 before penetrating the graft 54. For example, where the fastener 34 is a staple having two tines, the tines may straddle a wire or other element of the stent 56, such that a part of the stent 56 is stapled to the graft 54 as the graft 54 is stapled to the aorta 70. Alternately, the stent 56 is fixed to the graft 54 via hooks, barbs or other engagement features, and the head 4 deploys one or more fasteners 34 through the graft 54, without additionally securing the stent 56 to the graft 54. The fasteners 34 securely fix the graft 54 to the aorta 70. Advantageously, the tip or tips of the fastener 34 may have a diameter small enough to slip between the threads of the weave of the graft 54, minimizing any leakage through the graft 70.

As shown in FIG. 10, the functions of sealing and fixation are substantially separated. That is, the expansion of the stent 56 substantially seals the graft 54 to the aorta 70, and deployment of the fasteners 34 through the graft 54 and into the wall of the aorta 70 fixes the graft 54 to the aorta 70. Alternately, the functions of sealing and fixation need not be separated.

Next, the head 4 may be moved in any suitable manner to a different location on the graft 54, and another fastener 34 may be deployed. As one example, the head 4 may be moved relative to the shaft 6 about the joint 8. As another example, the shaft 6 may be rotated or otherwise moved, causing the head 4 to move as well. A number of fasteners 34 may be deployed to fix the graft 54 to the aorta 70. For example, fasteners 34 may be deployed substantially circumferentially around the distal end of the graft 54, retrograde to the aneurysm in the aorta 70. After the graft 54 has been fixed to the aorta 70, the head 4 may be used to deploy fasteners 34 about one or more orifices between the aorta 70 and blood vessels extending to or from the aorta 70. In this way, the graft 54 can be fixed precisely relative to those blood vessels. As one example, four fasteners 34 may be deployed about an orifice between the aorta 70 and a blood vessel. Other numbers of fasteners may be used, if desired. The graft 54 may include at least one pre-defined opening in its side corresponding to the location of an orifice between the aorta 70 and a blood vessel intersecting the aorta 70, in which case the opening in the graft 54 is aligned with the corresponding orifice in the aorta 70 prior to deploying fasteners 34 through the graft 54 and into the wall of the aorta 70 in proximity to the orifice. Alternately, the graft 54 is first fastened into contact with the aorta 70 in proximity to an orifice, and an RF probe or other tools is used to create an opening in the graft 54 at the orifice to allow blood to flow through it. In this way, the graft 54 is customized to a particular patient's anatomy, and the graft 54 need not be aligned relative to the blood vessels that connect to the aorta 70 before the graft 54 is fixed to the aorta 70.

Figure 11:
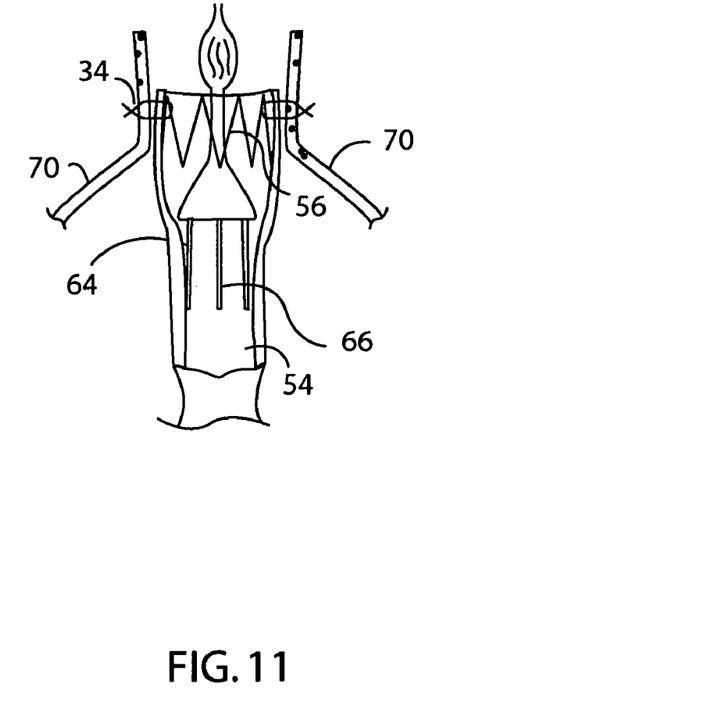
FIG. 11 is a side view of a fifth and final step of deploying an AAA graft.
Figure 12A:
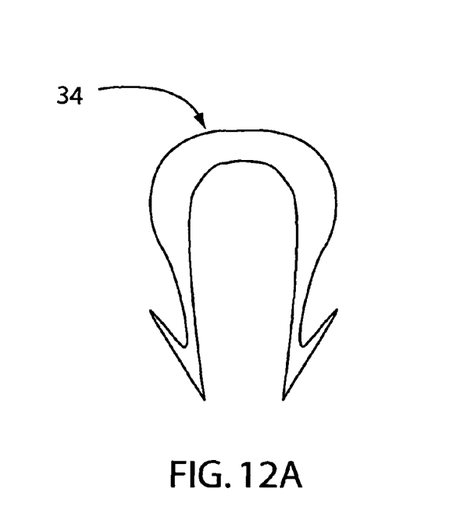
FIG. 12 is a collection of views of exemplary staples that may be deployed in the fourth step illustrated in FIG. 10.
Figure 12B:
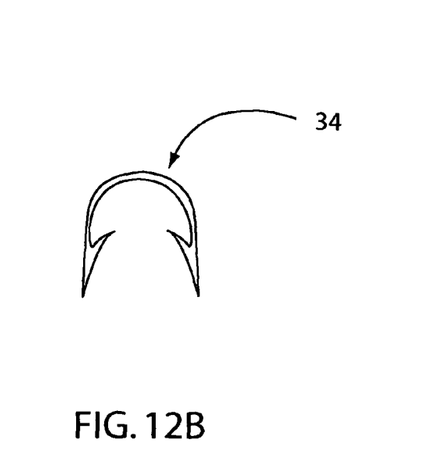
Figure 12C:
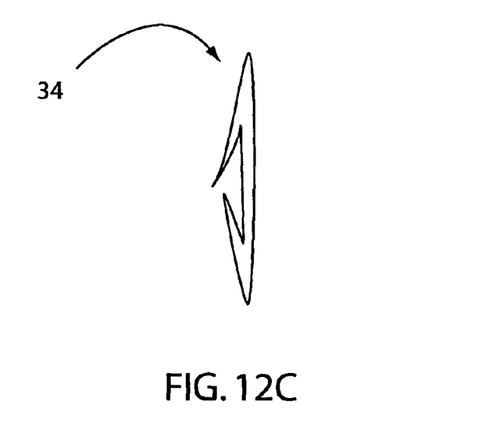
Figure 12D:
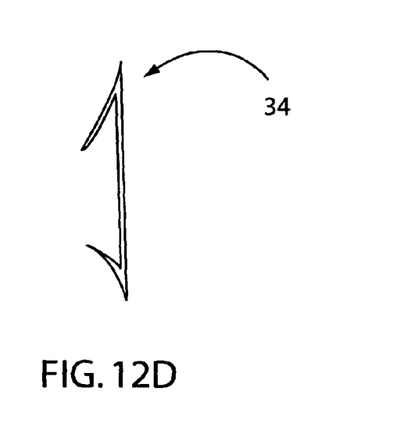
Figure 12E:
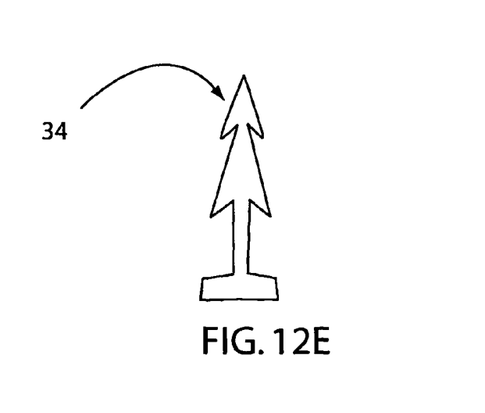
Figure 12F:
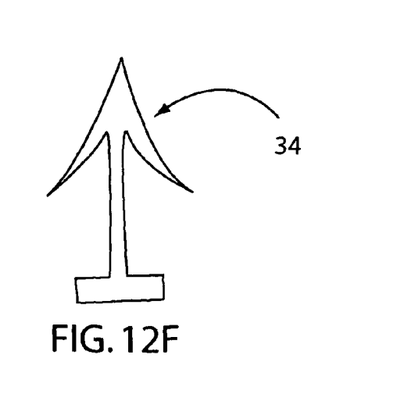

Referring also to FIG. 11, the strut or struts 60 that connect the stent 56 to the nosecone 58 are fractured. Alternately, the stent 56 and the nosecone 58 are separated in any suitable manner. The balloon 62 is then deflated. Alternately, the balloon 62 is deflated before the stent 56 is disconnected from the nosecone 58. Optionally, the sheath 64 may be advanced distally over the nosecone 58 and the balloon 62. The nosecone 58 and the balloon 62 are then withdrawn from the aorta 70 and from the patient's vasculature. The guidewire 66 is then withdrawn from the patient as well, and the procedure is complete.

The fastening tool 2 may be used for any other suitable application in a patient, whether in the aorta 70, a different portion of the vasculature, or outside the vasculature altogether. The fastening tool 2 need not be used in conjunction with the graft 54 and/or stent 56.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Further, the invention is not limited to the placement of an AAA graft. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A method for attaching a structure to a body lumen, comprising:
   providing a surgical tool comprising
      a plurality of substantially flat staples,
      a head holding said staples, said staples arranged in a stack therein, wherein said stack is biased distally, a shaft, a joint connecting said head to said shaft, wherein said joint allows said head to pivot to a position in which the longitudinal centerline of said head is angled relative to the longitudinal centerline of said shaft, and a driver slidable within said head;

providing a graft assembly, said graft assembly including a graft connected to a stent and a nose cone affixed to said stent by a plurality of struts;

inserting said graft, stent and surgical tool into the body lumen;

pivoting said head relative to said shaft such that the distal end of said head contacts the interior of said stent;

splaying at least one said staple within said body lumen, after said inserting;

after said splaying, reciprocating said driver to deploy serially the distalmost said staple in said stack through said stent into the body lumen; and after said reciprocating, frangibly separating said nose cone and said stent.

2. The method of claim 1, further comprising stabilizing said shaft before said deploying.

3. The method of claim 1, further comprising, after said deploying, moving said head to a different position along the perimeter of said stent and repeating said deploying.

4. The method of claim 3, wherein said moving comprises moving said head relative to said shaft.

5. The method of claim 1, further comprising providing a catheter having a lumen;

advancing said catheter into said body lumen; and advancing said surgical tool and said graft assembly through said lumen of said catheter, wherein said lumen of said catheter has a diameter no greater than 14 French.

6. The method of claim 1, wherein said graft assembly includes a sheath positioned around said graft and said stent, further comprising retracting said sheath before said deploying.

7. The method of claim 1, further comprising creating an opening in said graft.

8. The method of claim 1, wherein said frangibly separating comprises breaking said struts.

* * * * *